United States Patent [19]

Igarashi et al.

[11] 4,358,585
[45] Nov. 9, 1982

[54] 5-DEOXYAPRAMYCIN

[75] Inventors: Kikuo Igarashi, Itami; Tsunetoshi Honma, Ikoma; Tamio Sugawara, Mino, all of Japan

[73] Assignee: Shionogi & Co., Ltd., Osaka, Japan

[21] Appl. No.: 313,972

[22] Filed: Oct. 22, 1981

[30] Foreign Application Priority Data

Oct. 24, 1980 [JP] Japan .............................. 55/149821

[51] Int. Cl.$^3$ ........................................... C07H 15/22
[52] U.S. Cl. .................................. 536/16.8; 536/17.4
[58] Field of Search ........................... 536/4, 17 R, 18

[56] References Cited

PUBLICATIONS

O'Connor et al., "Chem. Abst.", vol. 85, 1976, p. 21760(t).

Primary Examiner—Johnnie R. Brown
Attorney, Agent, or Firm—Wenderoth, Lind & Ponack

[57] ABSTRACT

Novel 5-deoxyapramycin having the reinforced antimicrobial activity against gram-positive and negative bacteria with less side effects, resulted from reductive removal of 5-hydroxy group of apramycin through halogenation.

1 Claim, No Drawings

5-DEOXYAPRAMYCIN

BACKGROUND OF THE INVENTION

Chemical modifications of amino glycoside antibiotics have been investigated intensively to reinforce antimicrobial action and reduce side effects. The present inventors have found that the antimicrobial action of apramycin (for example, described as nebramycin factor II in Jap. Patent Publication No. 51-32719) is reinforced by substitution of 5-hydroxy group with a hydrogen, and have accomplished this invention.

SUMMARY OF THE INVENTION

The present invention relates to novel 5-deoxyapramycin represented by the following formula (I).

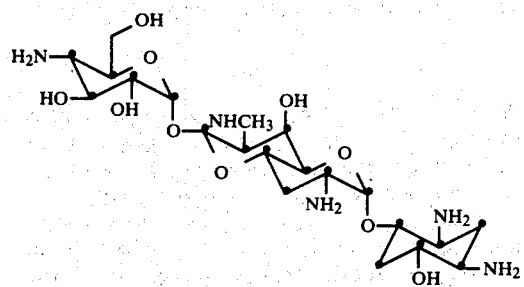

In the present invention the 5-deoxyapramycin represented by the formula (I) includes free bases and their salts, and in particular the pharmaceutically acceptable non-toxic acid addition salts. The acids which can form the acid addition salts are inorganic acids such as hydrochloric acid, hydrobromic acid, hydroiodic acid, sulfuric acid, phosphoric acid, and carbonic acid and organic acids such as acetic acid, fumaric acid, malic acid, tartaric acid, maleic acid, citric acid, mandelic acid, ascorbic acid, and gallic acid.

The compound (I) of the present invention is produced according to the following reaction sequence.

(Reaction sequence)

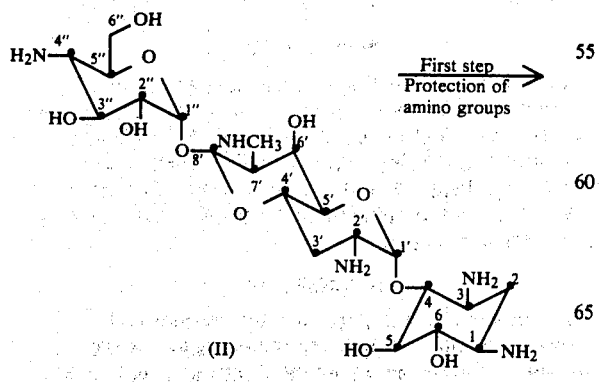

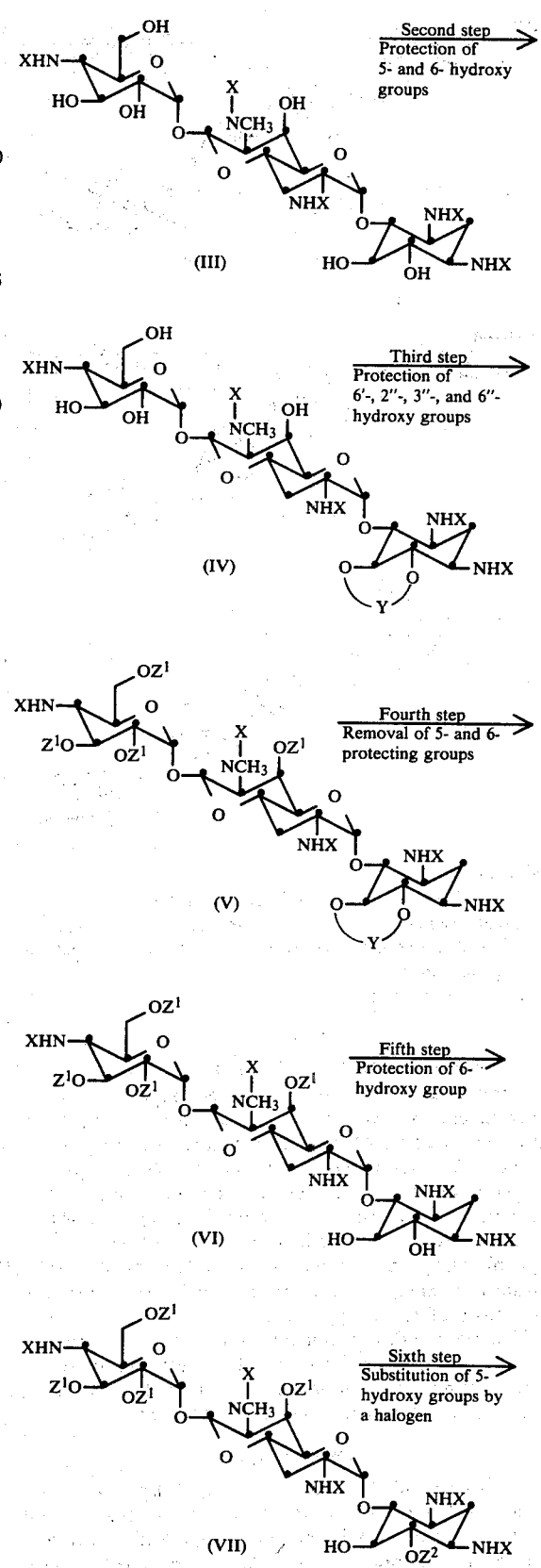

-continued
(Reaction sequence)

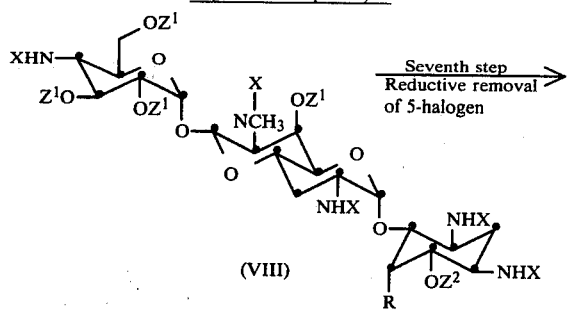

(VIII)

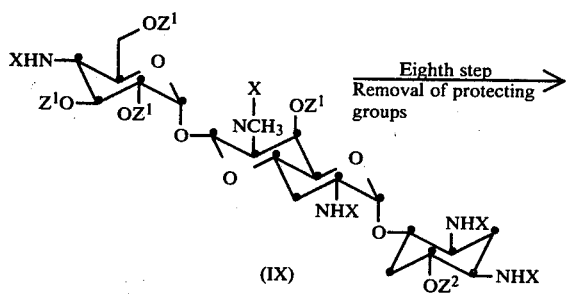

(IX)

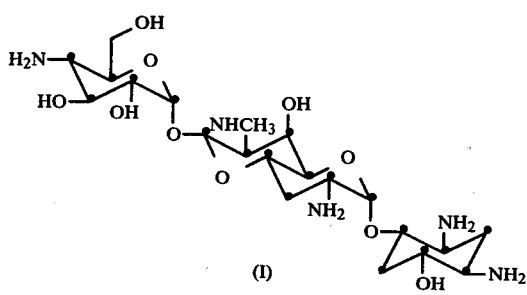

(I)

Wherein,
X represents an amino protecting group;
Y representing a cyclic hydroxy protecting group;
$Z^1$ and $Z^2$ each represents a hydroxy protecting group; and
R represents a halogen.

(First step)

In this step the 1-, 3-, 2'-, 7'-, and 4"-amino groups of apramycin are protected. As protecting groups to be introduced, the groups which can easily be removed after termination of the reaction are preferably employed. For example, the groups such as benzyloxycarbonyl in which the benzene nucleus may be substituted properly, formyl, t-butyloxycarbonyl, t-amyloxycarbonyl, methoxycarbonyl, ethoxycarbonyl, p-toluenesulfonyl, phthaloyl, m-nitrophenylthio, and triphenylmethylthio are examplified, and particularly benzyloxycarbonyl is preferably employed.

The method of introducing such protecting groups is known and in case of introducing benzyloxycarbonyl as a protecting group more than 5 equivalents of carbobenzoxy chloride may be used in the reaction.

(Second step)

In this step the 5- and 6-hydroxy groups are protected. As protecting groups the groups which are condensed with 5- and 6-hydroxy groups to form cyclic groups are preferably employed. For example, cyclohexanone dialkylketal, dialkoxypropane, etc. can be employed as protecting agents and preferably cyclohexanone dimethylketal is employed. The protecting agents are used in the reaction in excess to protect 2"-, 3"-, and 6"-hydroxy groups at the same time with the 5- and 6-hydroxy groups and then the protecting groups introduced at the position of 2", 3", and 6" are removed selectively by hydrolysis with a weak acid such as acetic acid to give the 5,6-protected compound.

This step is effected in conventional manners in the field of sugar chemistry and may be achieved in proper inert solvents (e.g., benzene, toluene, xylene, etc.) in the presence of a catalytic amount of acids (e.g., formic acid, acetic acid, p-toluenesulfonic acid, etc.).

(Third step)

In this step the 6'-, 2"-, 3"-, and 6"-hydroxy groups are protected. The protecting groups to be introduced are the groups which can easily be removed after termination of the reaction, e.g., formyl, acetyl, etc. and the reaction may be carried out in a conventional manner. For example, in case of introducing acetyl more than 4 equivalents of acetic anhydride may be used in the reaction.

(Fourth step)

In this step the 5- and 6-protecting groups introduced in the second step are removed and the reaction may be achieved through hydrolysis with an acid. Available acids are inorganic acids such as hydrochloric acid, sulfuric acid, phosphoric acid, etc. and organic acids such as formic acid, acetic acid, etc., out of which suitable one may be chosen preferably according to the kind of protecting groups.

(Fifth step)

In this step the 6-hydroxy groups is protected and the reaction may be carried out according to the third step; in the reaction 1 equivalent of the protecting agent is used. The compound of which the 5-hydroxy group is protected is produced as a by-product, so the 6-protected compound may be seperated preferably in conventional manners such as chromatography.

(Sixth step)

In this step the 5-hydroxy group is substituted by a halogen and the reaction may be achieved in conventional manners. As halogenating agents, hydrogen halide, phosphorus halide, bromine or iodine and phosphorus, thionyl chloride, and sulfuryl chloride are examplified, and particularly sulfuryl chloride is preferably employed in order to substitute 5-hydroxy group by a chlorine.

(Seventh step)

In this step the 5-halogen introduced in the sixth step is reductively removed, and the reaction may easily be achieved in the presence of tri-n-butyltin hydride. This reaction is preferably carried out in hydrocarbon solvents (e.g., benzene, toluene, etc.) and if necessary in the presence of an initiator for radical reaction such as azobisisobutyronitrile.

(Eighth step)

In this step the amino protecting groups and the hydroxy protecting groups are removed and the reaction may be achieved in conventional manners such as hydrolysis and catalytic hydrogenation. For example, if the amino protecting group is benzyloxycarbonyl and the hydroxy protecting group is acetyl, the amino protecting group may be removed by catalytic hydrogenation using palladium-carbon as a catalyst and then the hydroxy protecting group is removed by hydrolysis with an alkali.

The 5-deoxyapramycin and their non-toxic salts in the present invention have superior antimicrobial activities and display more potent effects against some kinds of gram-positive and negative bacteria than apramycin. The minimum inhibitory concentrations (MIC, μg/ml) of 5-deoxyapramycin and apramycin are shown as follows.

| | Compound | |
|---|---|---|
| Name of bacteria | 5-Deoxy-apra-mycin | Apra-mycin |
| Staphylococcus aureus AP01, AAD(4') | 3.13 | 6.25 |
| Staphylococcus aureus ATCC 25923 | 1.56 | 1.56 |
| Staphylococcus aureus No. 74 | 1.56 | 3.13 |
| Staphylococcus epidermidis ATCC 14990 | 0.39 | 0.39 |
| Staphylococcus epidermidis TB-172 | 0.39 | 0.39 |
| Escherichia coli W677/R5HL · AAC(6')-4 | 6.25 | 6.25 |
| Escherichia coli W677/JR88 · AAC(3)-I | 6.25 | 12.5 |
| Escherichia coli W677/JR76 · 2APH(3')-II + AAD(2") | 6.25 | 12.5 |
| Escherichia coli W677/JR214AAD(2") | 3.13 | 6.25 |
| Pseudomonas aeruginosa 3796 AAC(6')-3 | 6.25 | 12.5 |
| Pseudomonas aeruginosa PP-6 | 3.13 | 3.13 |
| Proteus rettgeri RET-29 | 0.78 | 1.56 |
| Proteus inconstans In-23 | 0.78 | 1.56 |
| Proteus vulgaris ATCC 6390 | 1.56 | 3.13 |
| Proteus vulgaris TB-708 | 1.56 | 3.13 |
| Proteus mirabilis Pm-71 | 1.56 | 3.13 |
| Serratia marcescens ATCC-13880 | 6.25 | 3.13 |
| Serratia marcescens MA-48 | 12.5 | 25 |
| Enterobacter cloacae Cl-126 | 1.56 | 3.13 |
| Citrobacter freundii Ct-27 | 1.56 | 3.13 |
| Klebsiella pneumoniae ATCC-27736 | 1.56 | 3.13 |
| Klebsiella pneumoniae Kl-159 | 25 | 50 |
| Moraxella villon AAC(6')-2 | 3.13 | 6.25 |

Notes:
* Observed in accordance with the standard method for determination of MIC[(1)(2)] regulated by Japan Society of Chemotherapy. Wherein the disc for antibiotic sensitivity testing [Modified Mueller Hinton medium] is used as a test medium.
* Cultured at 37° C. for 17 hours.
* The volume of bacteria for innoculation is $10^6$ CFU/ml.
(1) Chemotherapy 16(1), 98-99, 1968
(2) Chemotherapy 22(6), 1126-1128, 1974

As shown in the above table the compound (I) of the present invention have potent antimicrobial activities against gram-positive and negative bacteria and is useful as chemicals for medical and animal use. For example, the compound is used for treatment and preventation of various infections caused by Serratia marcescens, Proteus rettgeri, etc. Additionally the compound (I) of the present invention can be added to perishable foods as a bactericide and moreover applied to places and implements where bacteria are possibly existent as a disinfectant.

The compound (I) of the present invention can be administered to human and other animals orally or parenterally. Particularly the pharmacologically acceptable salts (e.g., sulfate) can be administered by means of intravenous injection, intramuscular injection, or subcutaneous injection as aqueous solutions. The compound (I) may be placed in tightly closed ampouls as solutions, preferably preserved in ampouls or vials as crystals, powders, fine crystals, lyophilizate, etc., and dissolved before use. Stabilizer may also be added.

In this connection the compound (I) together with pharmaceutical components such as diluents (e.g., starch, sucrose, lactose, calcium carbonate, kaolin, etc.), extending agents (e.g., lactose, starch, calcium carbonate, calcium phosphate, kaolin, bentonite, talc, etc.), lubricants (e.g., stearic acid, paraffin, boric acid, silica, sodium benzoate, polyethylene glycol, etc.), and so on may be formulated into powders, tablets, granules, capsules, troches, dry syrups, suppositories, suspensions, emulsions, inhalants, eye drops, powders for local administration, ointments, etc. and administered. In application for treatment of sensitive infections of human or animals, the compound (I) may be administered at a daily dose of 0.01-5 g/kg in injection, preferably 0.02-0.2 g/kg, 0.01-10 g/kg in oral administration, preferably 0.05-0.5 g/kg, and 0.01-10 g/kg in local administration, preferably 0.05-0.5 g/kg, respectively every 3-12 hours. The dosage, however, may be increased or decreased according to sensitivity of pathogenic bacteria, frequency of administration, and the condition of a patient.

The following example will demonstrate the present invention more in detail.

EXAMPLE (a) 1,3,2',7',4'''-Penta-N-benzyloxycarbonylapramycin (III: X=PhCH$_2$OCO)

Apramycin ½ hydrate (10.000 g, 18.23 m mole) is dissolved in water (150 ml), to which sodium carbonate (10.47 g, 94.79 m mole) and acetone (100 ml) are added to give a homogeneous mixture. To the mixture carbobenzoxy chloride (14.63 ml, 102.1 m mole) is dropwise added over 15 minutes under vigorous stirring under cooling at −5°−−1° C., and after stirring for 2.5 hours at room temperature the reaction mixture is poured into ice water (800 ml). The resultant precipitate is filtered, washed with water, and dissolved in methanol (100 ml), which is distilled off under reduced pressure after decolorization with active carbon (3 g). Ether is added to the obtained residue and the wall of the tube is rubbed with a metal stick. The precipitating powder is filtered, washed with ether, and dried on phosphorus pentoxide under reduced pressure to give the title compound. (22.134 g, yield: 100%). A part of this compound is chromatographed on a column [adsorbent: Kiesel gel 60 (made by Merck & Co.); eluent: chloroform-methanol (97:3)], pure fractions are collected, the solvents are evaporated under reduced pressure, and the residue is treated with methanol. ether to give powder.

$[\alpha]_D^{23.0} \pm 68.1 \pm 1.0°$ (c=1.037, CH$_3$OH)

IR: $\nu_{max}^{KBr}$ 3406, 1700, 1520 cm$^{-1}$.

Elemental analysis Calcd. (for C$_{61}$H$_{71}$N$_5$O$_{21}$.H$_2$O) (%): C, 59.65; H, 5.99; N, 5.70. Found. (%): C, 59.64; H, 5.87; N, 5.70.

(b)
1,3,2',7',4'''-Penta-N-benzyloxycarbonyl-5,6-O-cyclohexylideneapramycin

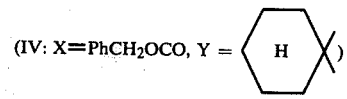

(IV: X=PhCH$_2$OCO, Y = cyclohexylidene)

The product from (a) (22.134 g, 18.23 m mole) is dissolved in dimethylformamide (630 ml), cyclohexanone dimethylketal (37 ml, 248.9 m mole) and p-toluenesulfonic acid (2.128 g) are added, and the mixture is stirred under reduced pressure of 25 mm Hg under heating at 50° C. for 3 hours and then neutralized with triethylamine (1.61 ml). After evaporation of the solvent, the residue (33.1 g) is dissolved in ethyl acetate (300 ml), washed with water, dried on sodium sulfate, and then evaporated under reduced pressure. Thus obtained white powder (25.13 g) is dissolved in 80% acetic acid (210 ml), kept at room temperature for 45 minutes, and then poured in ice water (1 L). The resultant precipitate is filtrated, washed with water, and dissolved in ethyl acetate. The mixture is washed with water, dried on sodium sulfate, and evaporated under reduced pressure. The residue (23.60 g) is chromatographed on a column [adsorbent: Kiesel gel 60 (made by Merck & Co.) 800 g; eluent: chloroform~chloroform-acetone (99:1~66:40)]. Each fraction is checked by thin layer chromatography, the fractions showing multi-spots are further chromatographed on a column repeatedly in the same manner, and the fractions showing a single spot are collected and crystallized from methanol to give the title compound as a pure product (13.893 g, yield: 59.1%).

mp. 140°-143° C.
$[\alpha]_D^{25} +63.7\pm 1.0°$ (c=1.034, $CH_3COOC_2H_5$)
IR: $\nu_{max}^{KBr}$ 3400, 1703, 1518 $cm^{-1}$.
Elemental analysis Calcd. (for $C_{67}H_{79}N_5O_{21}.2H_2O$) (%): C, 60.67; H, 6.31; N, 5.28. Found. (%): C, 60.44; H, 6.09; N, 5.30.

(c)
6',2'',3'',6''-Tetra-O-acetyl-1,3,2',7',4''-penta-N-benzyloxycarbonyl-5,6-O-cyclohexylideneapramycin

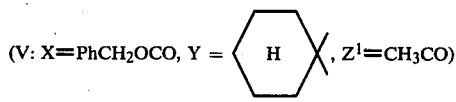

(V: X=PhCH$_2$OCO, Y = ⟨H⟩, Z$^1$=CH$_3$CO)

The product from (b) (7.000 g, 5.425 m mole) is dissolved in pyridine (91 ml) to which acetic anhydride (20.4 ml) is added, kept at room temperature for 24 hours, and poured in ice water. The precipitate is filtrated, washed with water, and dissolved in chloroform, and the mixture is washed with water, dried on sodium sulfate, and evaporated under reduced pressure. The residue (7.80 g) is dissolved in chloroform and hexane is added thereto. The resultant precipitate is filtrated to give the title compound (7.345 g, yield: 94.8%).
$[\alpha]_D^{25} +77.2\pm 1.1°$ (c=1.079, $CHCl_3$)
IR: $\nu_{max}^{KBr}$ 3440, 1745, 1724, 1515 $cm^{-1}$.
Elemental analysis Calcd. (for $C_{75}H_{87}N_5O_{25}$ .0.5-$H_2O$) (%): C, 61.38; H, 6.04; N, 4.77. Found. (%): C, 61.17; H, 5.86; N, 4.71.

(d)
6',2'',3'',6''-Tetra-O-acetyl-1,3,2',7',4''-penta-N-benzyloxycarbonylapramycin (VI: X=PhCH$_2$OCO, Z$^1$=CH$_3$CO)

The product from (c) (6.000 g, 4.114 m mole) is dissolved in 80% acetic acid (60 ml) and acetone (30 ml), heated at 70° C. for 6.5 hours, and poured in ice water. The resultant precipitate is filtrated, washed with water, and dissolved in ethyl acetate, and the mixture is washed with water, dried on sodium sulfate, and evaporated under reduced pressure. The residue (5.92 g) is dissolved in ethyl acetate and hexane is added thereto. The precipitate (5.60 g) is subjected to liquid chromatography [column: Prepack Column, size C (made by Merck & Co.)] and eluted with benzene-ethyl acetate (1:2) at a rate of 20 ml/fraction. The fractions No. 33-104 are collected, the solvent is evaporated under reduced pressure, the obtained residue is dissolved in chloroform, and hexane is added thereto to give the title compound (4.975 g, yield: 87%).
$[\alpha]_D^{25} +84.2\pm 1.3°$ (c=1.053, $CHCl_3$)
IR: $\nu_{max}^{KBr}$ 3400, 1747, 1724, 1518 $cm^{-1}$.
Elemental analysis Calcd. (for $C_{69}H_{79}N_5O_{25}.H_2O$) (%): C, 59.35; H, 5.85; N, 5.02. Found (%): C, 59.38; H, 5.61; N, 4.97.

(e) 6,6',2'',3'',6''-Penta-O-acetyl-1,3,2',7',4''-penta-N-benzyloxycabonylapramycin (VII: X=PhCH$_2$OCO, Z$^1$=Z$^2$=CH$_3$CO)

The product from (d) (1.000 g, 0.725 m mole) is dissolved in pyridine (10 ml) and cooled with ice, acetic anhydride (0.346 ml, 3.67 m mole) is added thereto, and the mixture is stirred at room temperature for 16 hours and 40 minutes. The reaction mixture is poured in ice water, and the resultant precipitate is filtrated, washed with water, dissolved in chloroform, dried on sodium sulfate, and evaporated under reduced pressure. The residue (1.075 g) is subjected to liquid chromatography [column: Prepack Column, size B; eluent: benzene-ethyl acetate (1:1); flow rate: 6 ml/min.; a fraction: 12 ml]. The fractions No. 22-50 are collected, the solvent is evaporated under reduced pressure, the obtained residue is dissolved in chloroform, and hexane is added thereto to precipitate the title compound (911 mg, yield: 88.5%).
$[\alpha]_D^{26} +75.4\pm 1.3°$ (c=1.033, $CHCl_3$)
Elemental analysis Calcd. (for $C_{71}H_{81}N_5O_{26}.H_2O$) (%): C, 59.28; H, 5.81; N, 4.87. Found. (%): C, 59.17; H, 5.81; N, 4.86.

(f)
6,6',2'',3'',6''-Penta-O-acetyl-1,3,2',7',4''-penta-N-benzyloxycarbonyl-5-chloro-5-deoxy-5-epiapramycin (VIII: X=PhCH$_2$OCO, Z$^1$=Z$^2$=CH$_3$CO, R=Cl)

The product from (e) (1.004 g, 0.698 m mole) is dissolved in pyridine (13 ml), to which sulfuryl chloride (0.231 ml, 2.85 m mole, 4.1 equivalents) is added under cooling at −20° C. Nine minutes later the reaction mixture is stirred at 0° C. for 3.5 hours, to which chloroform is added, and washed with 5% potassium hydrogensulfate, water, 5% sodium hydrogencarbonate, and water, respectively. The organic layer is dried on sodium sulfate and evaporated under reduced pressure. The residue (1.202 g) is dissolved in chloroform and hexane is added thereto. The obtained precipitate (1.027 g) is subjected to liquid chromatography [column: Prepack Column, size B; eluent: benzene-ethyl acetate (2:1); flow rate: 6 ml/min.; a fraction: 12 ml]. The fractions No. 56-69 are collected, and the solvent is evaporated under reduced pressure to give the title compound (388 mg, yield: 34.7%). The fractions No. 70-96 are collected, the solvent is distilled off, and the obtained residue (414 mg) is chromatographed on a column in the same manner as above to give the title compound (395 mg, yield: 35.3%).

Total weight 783 mg (yield: 70.0%).

A part of this compound is dissolved in chloroform, to which hexane is added, to precipitate for purification.
$[\alpha]_D^{24.0} +87.7\pm 1.2°$ (c=1.075, $CHCl_3$)
IR: $\nu_{max}^{KBr}$ 3407, 1746, 1726, 1516, 1500 $cm^{-1}$.

Elemental analysis Calcd. (for $C_{71}H_{80}ClN_5O_{25}.H_2O$) (%): C, 58.53; H, 5.67; Cl, 2.43; N, 4.81. Found. (%) C, 58.63; H, 5.51; Cl, 2.64; N, 4.90.

(g)

6,6′,2″,3″,6″-Penta-O-acetyl-1,3,2′,7′,4″-penta-N-benzyloxycarbonyl-5-deoxyapramycin (IX: $X=PhCH_2OCO$, $Z^1=Z^2=CH_3CO$)

The compound obtained in (f) (615 mg, 0.427 m mole) is dissolved in toluene (61.5 ml), tri-n-butyltin hydride (1.81 ml) and 2,2′-azobisisobutyronitrile (31 mg) are added thereto, and the reaction mixture is stirred at 90° C. for 1 hour and 40 minutes and evaporated under reduced pressure. The obtained residue (2.568 g) is washed with ether-hexane (1:1), and white powder is collected by filtration, washed with the same solvents, and subjected to liquid chromatography [column: Prepack Column, size B (made by Merck & Co.); eluent: benzene-ethyl acetate (2:1); flow rate: 6 ml/min.; a fraction: 12 ml)]. The fractions No. 56–105 are collected, the solvent is distilled off, and the residue (597 mg) is recrystallized from acetone-ether to give the title compound (430 mg, yield: 72.0%) as needles.

mp. 182°–184° C.
$[\alpha]_D^{23.5} + 89.7 \pm 1.3°$ (c=1.003, CHCl₃)
IR: $\nu_{max}^{KBr}$ 3340, 1735, 1704, 1514, 1502 cm⁻¹.
Elemental analysis Calcd. (for $C_{71}H_{81}N_5O_{25}.0.5H_2O$) (%): C, 60.33; H, 5.85; N, 4.95. Found. (%): C, 60.12; H, 5.75; N, 4.95.

The mother liquor giving the first crystal is subjected to recrystallization in the same manner to give the second crop of crystals (65 mg, yield: 10.9%).

mp. 180°–181.5° C.
Total weight 495 mg (yield: 82.9%)

(h) 5-Deoxyapramycin sulfate (sulfate of I)

To the product from (g) (465 mg, 0.331 m mole) and 10% palladium-carbon (120 mg), methanol (25 ml), water (3 ml), and concentrated hydrochloric acid (0.142 ml, 1.66 m mole) are added and the mixture is subjected to catalytic hydrogenation in H₂. Two hours later the catalyst is filtrated and washed with aqueous methanol, and the filtrate and the washing are combined and evaporated under reduced pressure. The obtained residue (321 mg) is dissolved in methanol (4.5 ml), and the mixed solution of 2 N sodium hydroxide (5 ml) and water (4.2 ml) is dropwise added over 7 minutes, and refluxed for 20 hours. The reaction mixture is cooled, neutralized by addition of concentrated hydrochloric acid (0.7 ml), adsorbed on an ion exchange resin Amberlite CG 50 (NH₄⁺, 120 ml), of which the column is washed with water (600 ml), and eluted with water (1 L) and 0.2 N ammonium hydroxide (1 L) by means of gradient method (a fraction: 13 ml). The fractions No. 107–116 are collected, and evaporated under reduced pressure. The residue is dissolved in water (8 ml), decolorized with active carbon, and filtrated with a glass filter (made by Millipore & Co.). The filtrate and the washing are combined and lyophilized, and thus obtained residue is kept in a desiccator containing sodium bromide (200 g) and water (100 g) until the residue absorbs moisture and becomes constant weight to give the objective title compound (228 mg, yield: 73.7%).

$[\alpha]_D^{23.5} + 108.3 \pm 1.5°$ (c=1.012, H₂O)

Elemental analysis Calcd. (for $C_{21}H_{41}N_5O_{10}.2.5H_2SO_4.9.5H_2O$) (%): C, 26.84; H, 6.97; N, 7.45; S, 8.53. Found (%): C, 26.75; H, 6.68; N, 7.45; S, 8.63.

NMR: % $\delta_{ppm}^{D_2O}$ 6.10 (d, $H_1'$ or $H_1''$ J=4 Hz), 6.03 (d, $H_1''$ or $H_1'$ J=4Hz), 3.47 (s, N—CH₃)

What is claimed is:

1. 5-Deoxyapramycin represented by the following formula and the pharmaceutically acceptable acid addition salts thereof

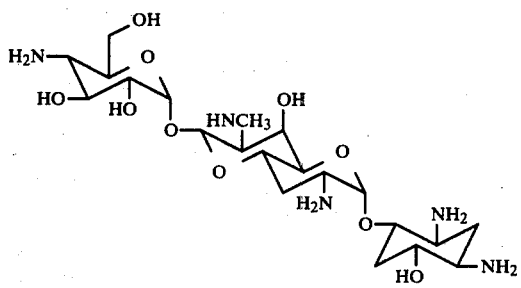

* * * * *